(12) United States Patent
Stahl et al.

(10) Patent No.: US 6,468,552 B1
(45) Date of Patent: Oct. 22, 2002

(54) STABILIZED COMPOSITIONS CONTAINING OXYGEN-LABILE ACTIVE AGENTS

(75) Inventors: Chris R. Stahl, San Pedro; Aldo O. Fernandez, Los Angeles; Frederick W. Woodin, Redondo Beach, all of CA (US)

(73) Assignee: Neutrogena Corporation, Los Angeles, CA (US)

( * ) Notice: Subject to any disclaimer, the term of this patent is extended or adjusted under 35 U.S.C. 154(b) by 0 days.

(21) Appl. No.: 09/586,583

(22) Filed: Jun. 2, 2000

(51) Int. Cl.$^7$ .................................................. A61K 7/00
(52) U.S. Cl. ....................................................... 424/401
(58) Field of Search ................... 424/401, 59

(56) References Cited

U.S. PATENT DOCUMENTS

| | | | |
|---|---|---|---|
| 3,755,560 A | 8/1973 | Dickert et al. | |
| 4,254,105 A | 3/1981 | Fukuda | |
| 4,421,769 A | 12/1983 | Dixon et al. | |
| 4,960,764 A | 10/1990 | Figueroa, Jr. et al. | |
| 5,424,082 A | 6/1995 | Dake et al. | |
| 5,484,816 A | 1/1996 | Yanagida et al. | 514/725 |
| 5,559,149 A | 9/1996 | Clum et al. | 514/529 |
| 5,646,186 A | 7/1997 | Wang et al. | 514/557 |
| 5,776,438 A * | 7/1998 | Tokue et al. | 424/59 |
| 5,780,086 A * | 7/1998 | Kirksey et al. | |
| 5,801,192 A | 9/1998 | Dumas et al. | |
| 5,976,555 A | 11/1999 | Liu et al. | 424/401 |
| 6,024,941 A | 2/2000 | Yanagida et al. | |
| 6,099,591 A * | 8/2000 | Matravers et al. | 8/408 |
| 6,106,846 A * | 8/2000 | Breton et al. | 424/401 |
| 6,139,872 A * | 10/2000 | Walsh | 424/464 |

FOREIGN PATENT DOCUMENTS

| | | |
|---|---|---|
| EP | 0165656 A | 12/1985 |
| WO | WO 96/07396 A | 3/1996 |
| WO | WO 96/31194 | 10/1996 |
| WO | WO 00/27353 | 5/2000 |

OTHER PUBLICATIONS

PCT International Search Report, PCT/US01/17739, Apr. 8, 2002.

Sagarin, Cosmetics, Science and Technology, 2$^{nd}$ Edition, vol. 1, 1972, pp. 32–43, 72–73.

Wenninger and McEWen, International Cosmetic Ingredient Dictionary and Handbook, The Cosmetic, Toiletry, and Fragrance Association, Washington, D.C., 7$^{th}$ Edition, 1997, pp. , 1626, 1650–1667, 1673–1686, 1693–1697.

McCutcheon's Detergents and Emulsifiers, North American Edition, MC Publishing Co., Glen Rock, NJ, 1986, pp.317–324.

Mezei et al., Liposomes–A Selective Drug Delivery System for the Topical Route of Administration: Gel Dosage Form, Journal of Pharmaceutics and Pharmacology, vol. 34 (1982), pp. 473–474.

Mezei, Liposomes as A Skin Drug Delivery System, Topics in Pharmaceutical Sciences, D.D. Breimer and P. Speiser eds., Elsevier Science Publishers B.V., NY, 1985, pp. 345–358.

Specification Erythorbic Acid, FCC Fine Granular. Chemicals for Food, Pharmaceutical, Cosmetic and Industrial Trades.

Erythorbic Acid, FCC IV, Monograph Specifications:134.

Calcium Pantothenate, Nutritional Agents and Vitamins, Martindale—the Extra Pharmacopoeia 30$^{th}$ Edition:1046.

Calcium Pantothenate, Merck Index 11$_{th}$ Edition:225.

Calcium Pantothenate, Remington—The Science and Practice of Pharmacy, 19$^{th}$ Edition.

Vitamin E The Protector, Biochemistry and Activity in Oral Supplements & Cosmetics, Roche Vitamins Inc.:1–8.

Actiquench ®GTP 20, Active Organics:1–5.

Mukhtar H., Katiyar S., Agarwal R. (1994) Green Tea and Skin—Anticarcinogenic Effects. The Journal of Invetigative Dermatology.102(1):3–7.

\* cited by examiner

*Primary Examiner*—Jose' G. Dees
*Assistant Examiner*—Konata M. George
(74) *Attorney, Agent, or Firm*—William E. McGowan

(57) ABSTRACT

The present invention relates to a composition (e.g., a cosmetic composition) comprising, (a) an oxygen labile active agent, (b) erythorbic acid or a cosmetically acceptable salt or ester thereof, (c) optionally, a tocopherol derivative, (d) optionally, a pantothenic acid derivative, and (e) optionally, an extract of green tea, provided that said composition comprises a compound selected from both (c) and (d), both (c) and (e), or both (d) and (e).

26 Claims, No Drawings

STABILIZED COMPOSITIONS CONTAINING OXYGEN-LABILE ACTIVE AGENTS

FIELD OF THE INVENTION

The present invention relates to compositions comprising an oxygen-labile active agent.

BACKGROUND OF THE INVENTION

It has become desirable to include various oxygen-labile active agents in topical skin care compositions in order to provide a cosmetic/therapeutic benefit, e.g., to the skin and hair. Examples of such active agents include, but are not limited to, vitamins such as Vitamin C, Vitamin K, and Vitamin A. Other active agents such as ubiquinone and hydroquinone can be used to reduce the appearance of aging, where due to the sun or time. Stabilizing such compositions containing oxygen-labile active agents, however, has been proven difficult as the active agents are often either combined with other compounds that may accelerate their decomposition or they are exposed to the environment (e.g., oxygen) over time.

The present invention relates to a method of stabilizing such oxygen labile active agents in order to provide compositions that contain oxygen-labile active agents (e.g., retinol) that are very stable over long periods of time.

SUMMARY OF THE INVENTION

The present invention features a composition comprising (a) an oxygen labile active agent, (b) erythorbic acid or a cosmetically acceptable salt or ester thereof, (c) optionally, a tocopherol derivative, (d) optionally, a pantothenic acid derivative, and (e) optionally, an extract of green tea, provided that said composition comprises a compound selected from both (c) and (d), both (c) and (e), or both (d) and (e) (e.g., either (i) both a tocopherol derivative and a pantothenic acid derivative, (ii) both a tocopherol derivative and an extract of green tea, or (iii) both a pantothenic acid derivative and an extract of green tea).

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments are to be construed merely to be illustrative and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference.

The present invention relates to a composition comprising, (a) an oxygen labile active agent, (b) erythorbic acid or a cosmetically acceptable salt or ester thereof, and (c) either (i) both a tocopherol derivative and a pantothenic acid derivative, (ii) both a tocopherol derivative and an extract of green tea, or (iii) both a pantothenic acid derivative and an extract of green tea.

In one embodiment, the composition comprises from about 0.001% to about 1% (e.g., about 0.2%), by weight, of said tocopherol derivative. In one embodiment, the composition comprises from about 0.001 to about 0.5% (e.g., 0.1%), by weight, of said pantothenic acid derivative. In one embodiment, the composition comprises from about 0.001% to about 1% (e.g., about 0.1%), by weight, of said extract of green tea. In one embodiment, the composition comprises from about 0.005% to about 0.5% (e.g., about 0.05%), by weight, of erythorbic acid or a cosmetically acceptable salt or ester thereof. In one embodiment, the composition comprises a tocopherol derivative, a pantothenic acid derivative, an extract of green tea, and erythorbic acid or a cosmetically acceptable salt or ester thereof.

The present invention further features a cosmetic composition comprising, (a) an oxygen labile active agent, (b) erythorbic acid or a cosmetically acceptable salt or ester thereof, (c) either (i) both a tocopherol derivative and a pantothenic acid derivative, (ii) both a tocopherol derivative and an extract of green tea, or (iii) both a pantothenic acid derivative and an extract of green tea, and (d) a cosmetically acceptable carrier. In one aspect, the cosmetic composition comprises tocopherol, pantothenic acid, extract of green tea, and erythorbic acid or a cosmetically acceptable salt or ester thereof.

What is meant by an "oxygen-labile active agent" is an active agent that degrades due to oxidation or in the presence of oxygen. What is meant by active agent is a compound that offers a cosmetic, pharmaceutical, or therapeutic benefit when applied to the skin of a mammal (e.g., when topically administering to the skin or hair of a human). Examples of oxygen-labile active agents include retinol, retinal, ascorbic acid, tocotrienol, hydroquinone, ubiquinone, and dihydrolipoic acid. The amount of oxygen-labile active agent in the composition will depend upon the active agent used and the desired therapeutic/cosmetic effect, and typically will range from about 0.001% to about 20% (e.g., from about 0.1% to about 10%), by weight, of the composition. In one embodiment the composition comprises from about 0.001% to about 1% (e.g., from about 0.01% to about 0.5%), by weight, of retinol.

What is meant by a tocopherol derivative is tocopherol (e.g., αtocopherol, βtocopherol, δtocopherol, and other isomers thereof) and cosmetically acceptable salts and esters thereof (e.g., tocopherol acetate thereof). All isomers are included for compounds (e.g., tocopherol) where no specific isomer is indicated.

What is meant by a pantothenic acid derivative is pantothenic acid and cosmetically acceptable salts (e.g., sodium pantothenate or calcium pantothenate) or esters thereof.

What is meant by extract of green tea is the solid extract (e.g., polyphenols) from the tea plant. The extract may be solubilized or dispersed in a liquid carrier such as water or organic solvents such as alcohols (e.g., ethanol) or glycols (e.g., butylene glycols). Examples of extracts of green tea include extracts from the green tea plants camellia oleifera and camellia sinensis.

The topical compositions useful in the present invention involve formulations suitable for topical application to skin. The compositions may be made into a wide variety of product types that include but are not limited to lotions, creams, gels, sticks, sprays, ointments, shampoos, pastes, mousses, and cosmetics. These product types may comprise several types of cosmetically acceptable carrier systems including, but not limited to solutions, emulsions, gels, solids and liposomes. What is meant by "cosmetically acceptable carrier" is a carrier that is capable of having the (a) oxygen-labile active agent, (b) erythorbic acid or a cosmetically acceptable salt or ester thereof, and (c) tocopherol derivative, pantothenic acid derivative, and/or extract of green tea, dispersed or dissolved therein, and of possessing acceptable safety properties (e.g., irritation and sensitization characteristics).

The topical compositions useful in the present invention formulated as solutions typically include an aqueous (e.g., water) or organic solvent (e.g., from about 80% to about 99.99% or from about 90% to about 99% of an acceptable aqueous or organic solvent). Examples of suitable organic solvents include: propylene glycol, polyethylene glycol (200–600), polypropylene glycol (425–2025), glycerol, 1,2, 4-butanetriol, sorbitol esters, 1,2,6-hexanetriol, ethanol, and mixtures thereof.

Topical compositions useful in the subject invention may be formulated as a solution comprising an emollient. Such compositions preferably contain from about 2% to about 50% of a an emollient(s). As used herein, "emollients" refer to materials used for the prevention or relief of dryness, as well as for the protection of the skin. A wide variety of suitable emollients are known and may be used herein. Sagarin, Cosmetics, Science and Technology, 2nd Edition, Vol. 1, pp. 32–43 (1972) and the International Cosmetic Ingredient Dictionary and Handbook, eds. Wenninger and McEwen, pp. 1656–61 1626, and 1654–55 (The Cosmetic, Toiletry, and Fragrance Assoc., Washington, D.C., $7^{th}$ Edition, 1997) (hereinafter "ICI Handbook") contains numerous examples of suitable materials.

A lotion can be made from a solution carrier system. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution carrier system is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution carrier system is an ointment. An ointment may comprise a simple base of animal or vegetable oils or semi-solid hydrocarbons (oleaginous, absorbent, emulsion and water soluble ointment bases). Ointments may also comprise absorption ointment bases that absorb water to form emulsions. Ointment carriers may also be water-soluble. An ointment may comprise from about 2% to about 10% of an emollient(s) plus from about 0.1% to about 2% of a thickening agent(s). A more complete disclosure of thickening agents or viscosity increasing agents useful herein can be found in Sagarin, Cosmetics, Science and Technology, 2nd Edition, Vol. 1, pp. 72–73 (1972) and the ICI Handbook pp. 1693–1697.

If the carrier is formulated as an emulsion, from about 1% to about 10% (e.g., from about 2% to about 5%) of the carrier system comprises an emulsifier(s). Emulsifiers may be nonionic, anionic or cationic.

Suitable emulsifiers are disclosed in, for example, U.S. Pat. No. 3,755,560, U.S. Pat. No. 4,421,769, McCutcheon's Detergents and Emulsifiers, North American Edition, pp. 317–324 (1986), and the ICI Handbook, pp.1673–1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s)

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type, as disclosed in U.S. Pat. No. 4,254,105, are also useful in the subject invention. In general, such single or multiphase emulsions contain water, emollients, and emulsifiers as essential ingredients. Triple emulsion carrier systems comprising an oil-in-water-in-silicone fluid emulsion composition as disclosed in U.S. Pat. No. 4,960,764 are also useful in the subject invention.

Liposomal formulations are also useful compositions of the subject invention. Such compositions can be prepared by first combining hesperetin with a phospholipid, such as dipalmitoylphosphatidyl choline, cholesterol and water according to the method described in Mezei & Gulasekharam, "Liposomes—A Selective Drug Delivery System for the Topical Route of Administration; Gel Dosage Form", Journal of Pharmaceutics and Pharmacology, Vol. 34 (1982), pp. 473–474, or a modification thereof. Epidermal lipids of suitable composition for forming liposomes may be substituted for the phospholipid. The liposome preparation is then incorporated into one of the above topical carrier systems (e.g., a gel or an oil-in-water emulsion) in order to produce the liposomal formulation. Other compositions and pharmaceutical uses of topically applied liposomes are described in Mezei, M., "Liposomes as a Skin Drug Delivery System", Topics in Pharmaceutical Sciences (D. D. Breimer and P. Speiser, eds.,), Elsevier Science Publishers B. V., New York, N.Y., 1985, pp. 345–358, incorporated herein by reference.

The topical compositions useful in the subject invention may contain, in addition to the aforementioned components, a wide variety of additional oil-soluble materials and/or water-soluble materials conventionally used in topical compositions, at their art-established levels. Various water-soluble materials may also be present in the compositions useful in the subject invention. These include humectants, proteins and polypeptides, preservatives and an alkaline agent. Examples of such agents are disclosed in the ICI Handbook, pp.1650–1667. In addition, the topical compositions useful herein can contain conventional cosmetic adjuvants, such as dyes, opacifiers (e.g., titanium dioxide), pigments and perfumes.

The compositions (e.g., the cosmetic compositions) of the present invention can be topically applied to the skin or hair of a mammal (e.g., by the direct laying on or spreading of the composition on the skin or hair of a human). Depending on the selection of the active agent (e.g., the oxygen-labile active agent or other active agents), the compositions can be used to treat a number of skin and hair disorders such as but not limited to acne, mottled hyperpigmentation, age spots, wrinkles, fine lines, cellulite, and other visible signs of aging (whether due to photoaging or chronoaging).

The composition and formulations containing such compositions of the present invention may be prepared using methodology that is well known by an artisan of ordinary skill. The following is a description of the manufacture of various compositions of the present invention. Other compositions of the present invention can be prepared in an analogous manner by a person of ordinary skill in the art.

EXAMPLE 1

MANUFACTURE OF EMULSION COMPOSITIONS CONTAINING RETINOL

Six formulations containing retinol (Example I–VI), as described in Table 1, were manufactured as set forth below.

TABLE 1

|  | Examples | | | | | |
| --- | --- | --- | --- | --- | --- | --- |
|  | I | II | III | IV | V | VI |
| Water Phase Ingredients | Weight Percentage | | | | | |
| Deionized water | 65.141% | 70.182% | 72.132% | 69.682% | 70.082% | 69.982% |
| Carbomer | 0.4% | 0.4% | 0.4% | 0.4% | 0.4% | 0.4% |
| Methyl paraben | 0.25% | 0.25% | 0.25% | 0.25% | 0.25% | 0.25% |
| Disodium edetate | 0.1% | 0.1% | 0.1% | 0.1% | 0.1% | 0.1% |
| Glycerin | 2% | 2% | 2% | 2% | 2% | 2% |
| Erythorbic acid | 0.05% | None | 0.05% | None | None | None |
| Oil Phase Ingredients | | | | | | |
| C12–15 alkyl benzoate | 2% | 2% | 2% | 2% | 2% | 2% |
| Neopentyl glycol/dioctanoate/diisostearate | 5% | 5% | 5% | 5% | 5% | 5% |
| Octyl methoxycinnamate | 7.5% | 7.5% | 7.5% | 7.5% | 7.5% | 7.5% |
| Avobenzone | 3% | 3% | 3% | 3% | 3% | 3% |
| Glyceryl stearate (and) PEG-100 stearate | 3.5% | 3.5% | 3.5% | 3.5% | 3.5% | 3.5% |
| Phenoxyethanol | 0.9% | 0.9% | 0.9% | 0.9% | 0.9% | 0.9% |
| Isopropyl paraben (and) isobutyl paraben (and) butyl paraben | 0.6% | 0.6% | 0.6% | 0.6% | 0.6% | 0.6% |
| Cetyl alcohol | 2.5% | 2.5% | 2.5% | 2.5% | 2.5% | 2.5% |
| Propyl paraben | 0.15% | 0.15% | 0.15% | 0.15% | 0.15% | 0.15% |
| Tocopheryl acetate | 0.5% | 0.5% | 0.5% | 0.5% | 0.5% | 0.5% |
| Phenyltrimethicone | 1% | 1% | 1% | 1% | 1% | 1% |
| Neutralization Ingredient | | | | | | |
| Sodium hydroxide (50% solution) | 0.24% | 0.24% | 0.24% | 0.24% | 0.24% | 0.24% |
| Post-addition Ingredients | | | | | | |
| Calcium pantothenate | None | None | None | None | 0.1% | None |
| α-Tocopherol | None | None | None | None | None | 0.2% |
| Camellia oleifera extract (and) water (and) trimethylpropane trioctanoate (and) glycerin (and) butylene glycol (and) calcium pantotenate (and) α-tocopherol | 5% | None | None | None | None | None |
| Camellia oleifera extract (and) water (and) butylene glycol | None | None | None | 0.5% | None | None |
| Retinol (and) polysorbate 20 | 0.169% | 0.178% | 0.178% | 0.178% | 0.178% | 0.178% |

The following procedure was used to make each of Examples I–VI. The deionized water was added to a primary container. To this primary container, the carbomer (Synthalen M®, 3V Inc., Weehawken, N.J.) was added under moderate mixing with a propeller. This mixing continued until there were no more lumps of carbomer. Subsequently, the primary container was heated to approximately 70–75° C., and the remaining water phase ingredients were then added.

In a second container, the oil phase ingredients were combined and heated to 70–75° C. The C12–15 alkyl benzoate was purchased from Finetex (Elmwood Park, N.J.) under the tradename FinsolvTN®, the Neopentyl glycol/dioctanoate/diisostearate was purchased from Bernel Chemical (Englewood, N.J.) under the tradename Minno 21®, the Glyceryl stearate (and) PEG-100 stearate was purchased from Unichema North America (Chicago, Ill.) under the tradename Arlacell165 ®, the Isopropyl paraben (and) isobutyl paraben (and) butyl paraben was purchased from Sutton Industries (Chatham, N.J.) under the tradename LiquaPar Oil®, and the Phenyltrimethicone was purchased from Dow Corning Corp. (Midland, Michigan) under the tradename Dow Corning 556®.

The oil phases ingredients were constantly mixed to ensure homogeneity. After both phases reached the requisite temperature of 70–75° C., the oil phase in the second container was slowly poured and mixed into the water phase in the primary container. After phasing, the mixture was allowed to mix for five minutes. Then the batch was neutralized with the sodium hydroxide to a pH between 6 and 7. The batch was then homogenized with a Gifford-Wood homogenizer Model #1 (Greerco Corp., Hudson, N.H.) for approximately one minute at a 70% speed. The batch was allowed to cool to 45–50° C., and the post-addition ingredients were then added. The retinol used was Retinol 50C which is available from BASF (Mt. Olive, N.J.). This means that the retinol was in a 50%/50% blend with polysorbate 20. Thus the actual amount of retinol in the formulation is 0.0825% retinol. The Camellia oleifera extract (and) water (and) trimethylpropane trioctanoate (and) glycerin (and) butylene glycol (and) calcium pantothenate (and) α-tocopherol was purchased from DC Inc. (South Plainsfield, N.J.) under the tradename DC1500 Anti Oxidant Blend®, and the Camellia oleifera extract (and) water (and) butylene glycol was purchased Active Organics (Dallas, Tex.) as Actiquench HTP-20®.

EXAMPLE 2
CHEMICAL STABILITY OF RETINOL

A study was conducted to determine the impact of the erythorbic acid, camellia oleifera extract, calcium pantothenate, and tocopherol on the stability of the oxygen labile active agent retinol. As depicted in Table 2, Examples I–VI comprised the following compounds, by weight.

TABLE 2

| Example | Erythorbic Acid | Camellia Oleifera | Calcium Pantothenate | α-Tocopherol |
|---------|-----------------|-------------------|----------------------|--------------|
| I       | 0.05%           | 0.1%              | 0.1%                 | 0.2%         |
| II      | NONE            | NONE              | NONE                 | NONE         |
| III     | 0.05%           | NONE              | NONE                 | NONE         |
| IV      | NONE            | 0.1%              | NONE                 | NONE         |
| V       | NONE            | NONE              | 0.1%                 | NONE         |
| VI      | NONE            | NONE              | NONE                 | 0.2%         |

All of the formulations were prepared and packaged in aluminum tubes that were purged with argon. This purging minimizes the presence of oxygen to maximize the chemical stability of retinol. The formulations were then exposed to difference storage conditions. The formulations were set up at room temperate ("RT") and 40° C. temperatures ("40° C."). Samples were taken each month for three months, and analyzed for retinol content. Table 3 shows the result of the analysis.

TABLE 3

% Retinol Loss From Initial Concentration

| Example | 1 Month RT | 1 Month 40° C. | 3 Month RT | 3 Month 40° C. |
|---------|------------|----------------|------------|----------------|
| I       | 0%         | 1%             | 0%         | 1%             |
| II      | 6%         | 15%            | 11%        | 18%            |
| III     | 7%         | 10%            | 5%         | 9%             |
| IV      | 6%         | 11%            | 11%        | 12%            |
| V       | 6%         | 16%            | 9%         | 27%            |
| VI      | 0%         | 11%            | 5%         | 20%            |

The placebo formulation (Example II) performed poorly, as after 3 months at 40° C., 18% of the initial concentration of retinol had degraded. Under the same conditions, the formulations containing only erythorbic acid (Example III), only camellia oleifera extract (Example IV), only calcium pantothenate (Example V), or only α-tocopherol (Example VI) performed equally poor, respectively degrading 9%, 12%, 27%, and 20%. However, when erythorbic acid, camellia oleifera extract, calcium pantothenate, and α-tocopherol were combined (Example I), the amount of retinol degradation unexpectedly was only a mere 1% under the same conditions and with no degradation after 3 months at room temperature.

It is understood that while the invention has been described in conjunction with the detailed description thereof, that the foregoing description is intended to illustrate, and not limit the scope of the invention, which is defined by the scope of the appended claims. Other aspects, advantages, and modifications are within the claims.

What is claimed is:

1. A method of administering an oxygen labile active agent to the skin, said method of comprising applying a composition comprising,
    (a) an oxygen labile active agent,
    (b) erythorbic acid or a cosmetically acceptable salt or ester thereof,
    (c) a tocopherol derivative,
    (d) optionally, a pantothenic acid derivative, and
    (e) optionally, an extract of green tea, provided that said composition comprises a compound selected from (d) and (e), wherein said composition comprises from about 0.001% to about 1%, by weight, of said tocopherol derivative.

2. A method of claim 1, wherein said composition comprises a pantothenic acid derivative and extract of green tea.

3. A method of claim 1, wherein said composition comprises from about 0.001% to about 0.5%, by weight, of said pantothenic acid derivative.

4. A method of claim 1, wherein said composition comprises from about 0.001% to about 1%, by weight, of said extract of green tea.

5. A method of claim 1, wherein said composition comprises from about 0.001% to about 0.5%, by weight, of erythorbic acid or a cosmetically acceptable salt or ester thereof.

6. A method of claim 2, wherein said composition comprises:
    (a) about 0.001 to about 20%, by weight, of an oxygen labile active agent,
    (b) about 0.001% to about 0.5%, by weight, erythorbic acid, and
    (c) about 0.1% to about 1%, by weight, of said tocopherol derivative;
    (d) about 0.001% to about 0.5%, by weight, of said pantothenic acid derivative; and
    (e) about 0.001% to about 1%, by weight, of said extract of green tea.

7. A method of claim 5, wherein said oxygen labile active agent is selected from the group consisting of retinol, retinal, ascorbic acid, tocotrienol, hydroquinone, ubiquinone, and dihydrolipoic acid.

8. A method of claim 6, wherein said oxygen labile active agent is selected from the group consisting of retinol, retinal, ascorbic acid, tocotrienol, hydroquinone, ubiquinone, and dihydrolipoic acid.

9. A method of claim 7, wherein said oxygen labile active agent is retinol.

10. A method of claim 8, wherein said oxygen labile active agent is retinol.

11. A method of claim 9, wherein said composition comprises from about 0.01% to about 1% by weight, of said retinol.

12. A method of claim 10, wherein said composition comprises from about 0.01% to about 1%, by weight, of said retinol.

13. A cosmetic composition for administering an oxygen labile active agent to the skin, said composition comprising,
    (a) an oxygen labile active agent,
    (b) erythorbic acid or a cosmetically acceptable salt or ester thereof,
    (c) a tocopherol derivative,
    (d) optionally, a pantothenic acid derivative, and
    (e) optionally, an extract of green tea, provided that said composition comprises a compound selected from both (c) and (d), both (c) and (e), or both (d) and (e), wherein said composition comprises from about 0.001% to about 1%, by weight, of said tocopherol derivative.

14. A method of claim 13, wherein said composition comprises a pantothenic acid derivative and extract of green tea.

15. A composition of claim 13, wherein said composition comprises from about 0.001% to about 0.5%, by weight, of said pantothenic acid derivative.

16. A composition of claim 13, wherein said composition comprises from about 0.001% to about 5%, by weight, of said extract of green tea.

17. A composition of claim 13, wherein said composition comprises from about 0.001% to about 0.5%, by weight, of erythorbic acid or a cosmetically acceptable salt or ester thereof.

18. A composition of claim 14, wherein said composition comprises:
(a) about 0.001% to about 20%, by weight, of an oxygen labile active agent,
(b) about 0.001% to about 0.5%, by weight, erythorbic acid, and
(c) about 0.1% to about 1%, by weight, of said tocopherol derivative;
(d) about 0.001% to about 0.5%, by weight, of said pantothenic acid derivative; and
(e) about 0.001% to about 1%, by weight, of said extract of green tea.

19. A composition of claim 17, wherein said oxygen labile active agent is selected from the group consisting of retinol, retinal, ascorbic acid, tocotrienol, hydroquinone, ubiquinone, and dihydrolipoic acid.

20. A composition of claim 18, wherein said oxygen labile active agent is selected from the group consisting of retinol, retinal, ascorbic acid, tocotrienol, hydroquinone, ubiquinone, and dihydrolipoic acid.

21. A method of claim 19, wherein said oxygen labile active agent is retinol.

22. A method of claim 20, wherein said oxygen labile active agent is retinol.

23. A composition of claim 21, wherein said composition comprises from about 0.001% to about 1%, by weight, of said retinol.

24. A composition of claim 22, wherein said composition comprises from about 0.001% to about 1%, by weight, of said retinol.

25. A method of claim 3, wherein said oxygen labile active agent is retinol.

26. A composition of claim 16, wherein said oxygen labile active agent is retinol.

* * * * *